United States Patent
Hada et al.

(10) Patent No.: US 9,568,405 B2
(45) Date of Patent: Feb. 14, 2017

(54) METHOD, APPARATUS, AND STRUCTURE FOR DETERMINING INTERPOSER THICKNESS

(71) Applicant: International Business Machines Corporation, Armonk, NY (US)

(72) Inventors: Sayuri Hada, Machida (JP); Akihiro Horibe, Yokohama (JP); Keiji Matsumoto, Yokohama (JP)

(73) Assignee: International Business Machines Corporation, Armonk, NY (US)

( * ) Notice: Subject to any disclaimer, the term of this patent is extended or adjusted under 35 U.S.C. 154(b) by 251 days.

(21) Appl. No.: 14/554,088

(22) Filed: Nov. 26, 2014

(65) Prior Publication Data

US 2015/0153406 A1 Jun. 4, 2015

(30) Foreign Application Priority Data

Nov. 29, 2013 (JP) .................................. 2013-247309

(51) Int. Cl.
*G01N 3/20* (2006.01)
*G01N 3/22* (2006.01)
(Continued)

(52) U.S. Cl.
CPC . *G01N 3/22* (2013.01); *G01L 1/26* (2013.01); *G01N 3/20* (2013.01); *G01N 25/16* (2013.01); *G01N 2203/0057* (2013.01)

(58) Field of Classification Search
CPC ......................................................... G01L 1/26
See application file for complete search history.

(56) References Cited

U.S. PATENT DOCUMENTS 8,344,260 B2  1/2013  Okazaki
2005/0039342 A1*  2/2005  Kirstine ................. G01B 5/068
                                                                   33/552

FOREIGN PATENT DOCUMENTS

JP  11066122 A  3/1999
JP  11260865 A  9/1999
(Continued)

OTHER PUBLICATIONS

Oda et al., "Analysis of Stress and Deflection of Printed Plate Board Using Multilayered Beam Theory", Transactions of the Japan Society of Mechanical Engineers (A), The Japan Society of Mechanical Engineers, Jul. 1993, vol. 59, No. 563, p. 203-208.
(Continued)

*Primary Examiner* — Manuel Rivera Vargas
(74) *Attorney, Agent, or Firm* — Robert J. Shatto (57) ABSTRACT

The present invention includes the following steps: setting the thickness of an interposer to an initial value; determining the axial force of the interposer and the radius of curvature of the warpage caused by the difference in the thermal expansion coefficients of the supporting substrate, the joined layer and the interposer at the set thickness; determining the absolute value of the stress on the chip-connecting surface of the interposer from the stress due to the axial force of the interposer and the stress due to the warpage using the determined axial force and the radius of curvature; determining whether or not the absolute value of the stress is within a tolerance; changing the thickness of the interposer by a predetermined value; and confirming the set thickness as the thickness of the interposer when the determined absolute value of the stress is within the tolerance.

13 Claims, 9 Drawing Sheets

(51) Int. Cl.
*G01L 1/26* (2006.01)
*G01N 25/16* (2006.01)

(56) References Cited

FOREIGN PATENT DOCUMENTS

| JP | 2003532280 A | | 10/2003 |
|---|---|---|---|
| JP | 2005215997 A | | 8/2005 |
| JP | 2006053747 A | | 2/2006 |
| JP | 2006278803 A | | 10/2006 |
| JP | 2006339423 A | * | 12/2006 |
| JP | 2011039741 A | * | 2/2011 |
| JP | 2011159870 A | | 8/2011 |
| JP | 2013191903 A | | 9/2013 |
| WO | 2009044699 A1 | | 4/2009 |

OTHER PUBLICATIONS

Japan Patent Application No. 2013-247309 entitled, "Method, Apparatus, and Structure for Determining Interposer Thickness", filed Nov. 29, 2013.

* cited by examiner

331
The Young's modulus ($E_S$, $E_C$, $E_I$) and thermal expansion coefficients ($\alpha_S$, $\alpha_C$, $\alpha_I$) of the supporting substrate, the joined layer and the interposer; the desired thicknesses ($t_S$, $t_C$) of the supporting substrate and the joined layer; and the set thickness ($t_I$) of the interposer are used to generate a system of equations derived from the continuity of the strain at the interface; the balance of axial force; and the balance of the bending moment for the supporting substrate, the joined layer, and the interposer.

332
The system of equations is solved for the axial force ($P_I$) of the interposer and the radius of curvature ($R_I$) of the warpage in order to calculate the axial force ($P_I$) of the interposer and the radius of curvature ($R_I$) of the warpage.

341
The stress ($P_I/b_It_I$) due to the axial force of the interposer is calculated by dividing the axial force ($P_I$) of the interposer by the desired width ($b_I$) of the interposer and the set thickness ($t_I$) of the interposer.

↓

342
The stress ($E_I(t_I/2)/R_I$) due to the warpage of the interposer is calculated by multiplying the Young's modulus ($E_I$) of the interposer by half of the set thickness ($t_I/2$) and then dividing the product by the radius of curvature ($R_I$) of the warpage of the interposer.

↓

343
The sum of the stress due to the axial force of the interposer and the stress due to the warpage is calculated ($P_I/b_It_I + E_I(t_I/2)/R_I$).

| Thickness of Supporting Substrate (μm) | Thickness of Interposer According to Present Technique (μm) | Thickness of Interposer According to FEM (μm) |
|---|---|---|
| 600 | 155 | 140 - 190 |
| 900 | 220 | 200 - 240 |
| 1200 | 290 | 270 - 330 |

1200

METHOD, APPARATUS, AND STRUCTURE FOR DETERMINING INTERPOSER THICKNESS

BACKGROUND OF THE INVENTION

The present invention relates to a mounting technique for integrated circuit (IC) chips (referred to below simply as "chips") and, more specifically, to determining the thickness of an interposer on which a chip is mounted.

In high heat density chip mounting, where a chip is laminated three-dimensionally and mounted using face-down bonding, a low-cost organic substrate is typically used (instead of an inorganic substrate such as a ceramic) as the supporting substrate on which the flip chip is mounted.

However, because of the significant difference in thermal expansion coefficients between a silicon flip chip and an organic substrate, the thermal stress due to the significant difference in thermal expansion coefficients may cause the solder-joined portion to be destroyed when an organic substrate is used.

Figure 1:
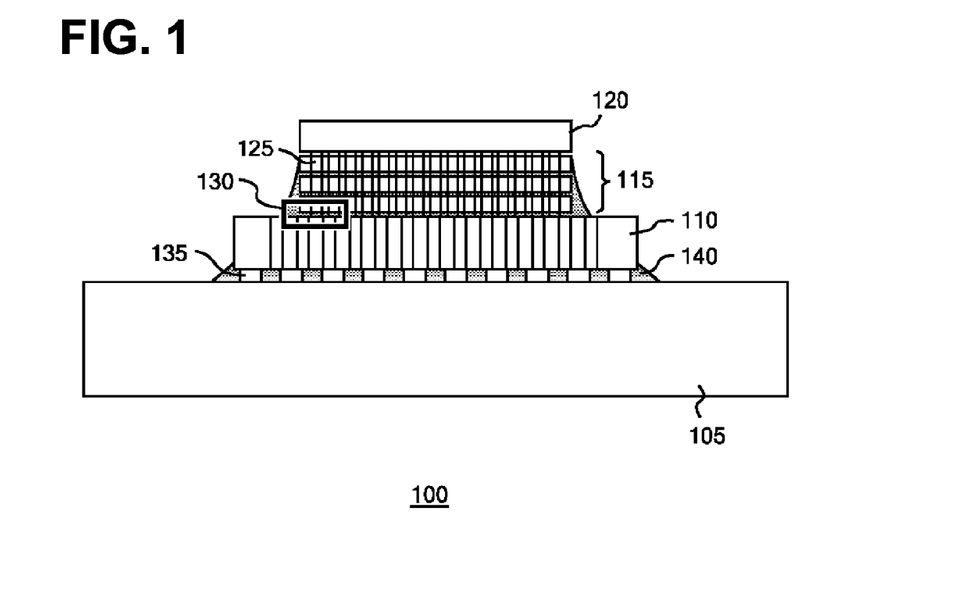
FIG. 1 is a simplified cross-sectional view of a chip mounting structure in which a chip is laminated and mounted on a supporting substrate and an interposer.

A mounting structure 100 is shown in FIG. 1. In this mounting structure 100, a silicon interposer 110 may be provided on an organic supporting substrate 105, and a silicon laminated chip 115 and top chip 120 may be mounted on the interposer 110. The top chip 120 is connected electrically on the obverse surface of the interposer 110 via a through-hole 125 provided inside the laminated chip 115. The reverse surface of the interposer 110 is connected to the supporting substrate 105 via electrodes 135, and an underfill 140 is provided between the supporting substrate 105 and the interposer 110. The joined portion 130 of the interposer 110 and the laminated chip 115 is more susceptible to destruction than other joined portions because it is closest to the supporting substrate 105, and the frequency of thermal stress occurring is highest when a number of chips are laminated individually.

Therefore, when an organic substrate with a high thermal expansion coefficient is used as a supporting substrate, a means of reducing the stress on the joined portion of the interposer and the chip is desired in order to perform chip mounting more reliably. The uppermost chip has been adjusted in order to reduce the stress on the joined portion, but this technique relies on the experience of the chip's designer. Because it relies on the experience of the designer, it is difficult to automate so that it can be performed by somebody other than the designer.

The laminated structure is optimized by directly determining the stress on the joined portion of the interposer and the chip in a laminated structure including a supporting substrate, an interposer, and a chip. The stress on the joined portion can be determined, for example, by performing a parameter analysis using the finite element method (FEM). This technique requires a high degree of expertise, and the modelling and calculations take time. Also, one-off calculations are essentially performed on each model, and this technique is difficult to automate so that it can be applied to different models.

SUMMARY

One aspect of the present invention is a method including the steps of: setting the thickness of an interposer to an initial value, where the interposer is connected via a joined layer to a supporting substrate; determining an axial force of the interposer and a radius of curvature of a warpage caused by a difference in thermal expansion coefficients of the supporting substrate, the joined layer, and the interposer at the set thickness; determining, using the determined axial force and radius of curvature, the absolute value of a first stress on a chip-connecting surface of the interposer from a second stress due to the axial force of the interposer and a third stress due to the warpage; determining whether the absolute value of the first stress is within a tolerance; changing the thickness of the interposer by a predetermined value, when the determined absolute value of the first stress is not within the tolerance, and repeating the steps of determining the axial force of the interposer and the radius of curvature, determining the absolute value of the first stress on the chip-connecting surface of the interposer, and determining whether the determined absolute value of the first stress is within the tolerance; and confirming, for the changed thickness of the interposer, that the determined absolute value of the first stress is within the tolerance.

In an embodiment of the present invention, the step of determining the axial force of the interposer and the radius of curvature of the warpage in this method further includes the steps of: generating a system of equations derived from the continuity of the strain at the interface for, the balance of axial force for, and the balance of the bending moment for the supporting substrate, the joined layer, and the interposer; and calculating the axial force and the radius of curvature of the warpage by solving the system of equations for an axial thrust of the interposer and the radius of curvature of the warpage. The system of equations is generated using the following: the Young's modulus and thermal expansion coefficient of the supporting substrate, the joined layer, and the interposer; the desired thickness of the supporting substrate and the joined layer; and the set thickness of the interposer.

In an embodiment of the present invention, the Young's modulus and the thermal expansion coefficient of the joined layer are the Young's modulus and the thermal expansion coefficient calculated from the metal properties of a complex between a metal joined portion and an underfill resin portion.

In an embodiment of the present invention, the step of determining the absolute value of the stress on the chip-connecting surface of the interposer in this method further includes the steps of: calculating the second stress due to the axial force of the interposer by dividing the axial force of the interposer by a desired width of the interposer and the set thickness; calculating the third stress due to the warpage of the interposer by multiplying the Young's modulus of the interposer by half of the set thickness, and dividing the product by the radius of curvature of the warpage of the interposer; and calculating the total of the second stress due to the axial force of the interposer and the third stress due to the warpage.

Another aspect of the present invention is a computer program executing in a computer the steps of: setting the thickness of an interposer to an initial value, where the interposer is connected via a joined layer to a supporting substrate; determining an axial force of the interposer and a radius of curvature of a warpage caused by a difference in thermal expansion coefficients of the supporting substrate, the joined layer, and the interposer at the set thickness; determining, using the determined axial force and radius of curvature, the absolute value of a first stress on a chip-connecting surface of the interposer from a second stress due to the axial force of the interposer and a third stress due to the warpage; determining whether the absolute value of the first stress is within a tolerance; changing the thickness of the interposer by a predetermined value, when the determined absolute value of the first stress is not within the tolerance, and repeating the steps of determining the axial force of the interposer and the radius of curvature, determining the absolute value of the first stress on the chip-connecting surface of the interposer, and determining whether the determined absolute value of the first stress is within the tolerance; and confirming, for the changed thickness of the interposer, that the determined absolute value of the first stress is within the tolerance.

Another aspect of the present invention is an interposer connected via a joined layer to a supporting substrate, the thickness of the interposer being determined by: setting the thickness of the interposer to an initial value; determining an axial force of the interposer and a radius of curvature of a warpage caused by a difference in thermal expansion coefficients of the supporting substrate, the joined layer, and the interposer at the set thickness; determining, using the determined axial force and radius of curvature, the absolute value of a first stress on a chip-connecting surface of the interposer from a second stress due to the axial force of the interposer and a third stress due to the warpage; determining whether the absolute value of the first stress is within a tolerance; changing the thickness of the interposer by a predetermined value, when the determined absolute value of the first stress is not within the tolerance, and repeating the steps of determining the axial force of the interposer and the radius of curvature, determining the absolute value of the first stress on the chip-connecting surface of the interposer, and determining whether the determined absolute value of the first stress is within the tolerance; and confirming, for the changed thickness of the interposer, that the determined absolute value of the first stress is within the tolerance.

In an embodiment of the present invention, determining the axial force of the interposer and the radius of curvature of the warpage further includes: generating a system of equations derived from the continuity of the strain at the interface for, the balance of axial force for, and the balance of the bending moment for the supporting substrate, the joined layer, and the interposer; and calculating the axial force and the radius of curvature of the warpage by solving the system of equations for an axial thrust of the interposer and the radius of curvature of the warpage. The system of equations is generated using the following: the Young's modulus and thermal expansion coefficient of the supporting substrate, the joined layer, and the interposer; the desired thickness of the supporting substrate and the joined layer; and the set thickness of the interposer.

In an embodiment of the invention, the Young's modulus and the thermal expansion coefficient of the joined layer are the Young's modulus and the thermal expansion coefficient calculated from the metal properties of a complex between a metal joined portion and an underfill resin portion.

In an embodiment of the invention, determining the absolute value of the stress on the chip-connecting surface of the interposer further includes: calculating the second stress due to the axial force of the interposer by dividing the axial force of the interposer by a desired width of the interposer and the set thickness; calculating the third stress due to the warpage of the interposer by multiplying the Young's modulus of the interposer by half of the set thickness, and dividing the product by the radius of curvature of the warpage of the interposer; and calculating the total of the second stress due to the axial force of the interposer and the third stress due to the warpage.

Another aspect of the present invention is a chip mounting structure including: a flip chip, an interposer whose obverse surface is connected to the flip chip, a supporting substrate connected to the reverse surface of the interposer, and a joined layer provided between the interposer and the supporting substrate. Here, the thickness of the interposer is determined by: setting the thickness of the interposer to an initial value; determining an axial force of the interposer and a radius of curvature of a warpage caused by a difference in thermal expansion coefficients of the supporting substrate, the joined layer, and the interposer at the set thickness; determining, using the determined axial force and radius of curvature, the absolute value of a first stress on a chip-connecting surface of the interposer from a second stress due to the axial force of the interposer and a third stress due to the warpage; determining whether the absolute value of the first stress is within a tolerance; changing the thickness of the interposer by a predetermined value, when the determined absolute value of the first stress is not within the tolerance, and repeating the steps of determining the axial force of the interposer and the radius of curvature, determining the absolute value of the first stress on the chip-connecting surface of the interposer, and determining whether the determined absolute value of the first stress is within the tolerance; and confirming, for the changed thickness of the interposer, that the determined absolute value of the first stress is within the tolerance.

In an embodiment of the present invention, in this chip mounting structure, determining the axial force of the interposer and the radius of curvature of the warpage further includes: generating a system of equations derived from the continuity of the strain at the interface for, the balance of axial force for, and the balance of the bending moment for the supporting substrate, the joined layer, and the interposer; and calculating the axial force and the radius of curvature of the warpage by solving the system of equations for an axial thrust of the interposer and the radius of curvature of the warpage. The system of equations is generated using the following: the Young's modulus and thermal expansion coefficient of the supporting substrate, the joined layer, and the interposer; the desired thickness of the supporting substrate and the joined layer; and the set thickness of the interposer.

In an embodiment of the present invention, in this chip mounting structure, the Young's modulus and the thermal expansion coefficient of the joined layer are the Young's modulus and the thermal expansion coefficient calculated from the metal properties of a complex between a metal joined portion and an underfill resin portion.

In an embodiment of the present invention, in this chip mounting structure, determining the absolute value of the stress on the chip-connecting surface of the interposer further includes: calculating the second stress due to the axial force of the interposer by dividing the axial force of the interposer by a desired width of the interposer and the set thickness; calculating the third stress due to the warpage of the interposer by multiplying the Young's modulus of the interposer by half of the set thickness, and dividing the product by the radius of curvature of the warpage of the interposer; and calculating the total of the second stress due to the axial force of the interposer and the third stress due to the warpage.

In an embodiment of the present invention, in the chip mounting structure, the interposer is a silicon interposer, and the supporting substrate is an organic substrate.

DETAILED DESCRIPTION

The following is a detailed description of an embodiment for carrying out the present invention. However, the following embodiment does not limit the present invention as described in the scope of the claims. Also, all combinations of characteristics explained in the embodiment are not necessarily required in the technical solution of the present invention. The present invention can be embodied in many different ways, and should not be construed as being limited to the content of the embodiment described below. In the explanation of the embodiment, all configurational components and elements that are identical to each other are denoted by the same reference numbers.

Figure 2:
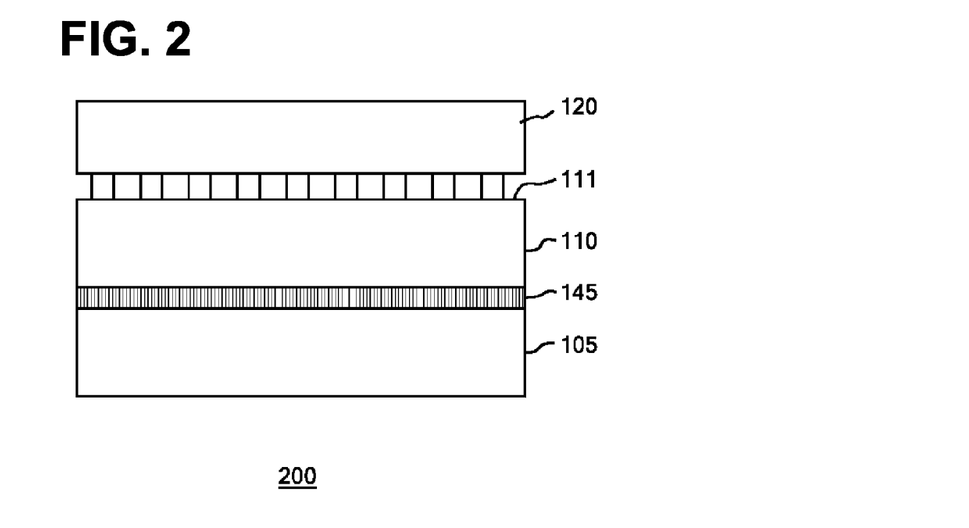
FIG. 2 is a simplified side view of the interposer being used in a chip mounting structure according to an embodiment of the present invention.

FIG. 2 is a simplified side view of the interposer 110 being used in a chip mounting structure 200 according to an embodiment of the present invention. The chip 120 is connected on the chip-connecting surface 111, or the obverse surface, of the interposer 110. The reverse surface of the interposer 110 is connected to the supporting substrate 105 via a joined layer 145. In accordance with the present embodiment, a thickness can be obtained for the interposer 110 which minimizes stress on the chip-connecting surface 111. The thickness can be obtained by analyzing the relationship between the stress on the chip-connecting surface 111 of the interposer 110 and the thickness of the interposer 110 using, for example, FEM.

Figure 3:
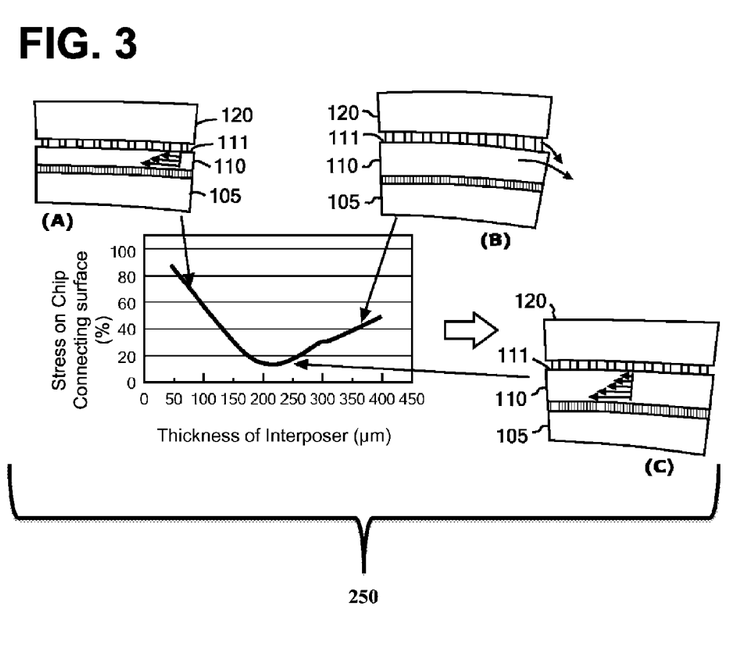
FIG. 3 is a graph showing the relationship between the thickness of the interposer and the stress on the chip-connecting surface.

FIG. 3 is a graph 250 showing the stress on the chip-connecting surface 111 when the thickness of a silicon interposer 110 is changed relative to an organic supporting substrate 105 and the joined layer 145. The stress on the chip-connecting surface 111 is indicated as a percentage (%) in comparison to a reference stress (the stress that occurs when the thickness of the supporting substrate 105 is 1200 μm and the thickness of the interposer 110 is 50 μm). As shown in (A) (see FIG. 3), the impact on the supporting substrate 105 becomes stronger as the thickness of the interposer 110 is reduced from 200 μm to 50 μm, and the stress (sometimes referred to as the "first stress") on the chip-connecting surface 111 increases. As shown in (B), the chip 120 no longer follows the warpage of the interposer 110 and the supporting substrate 105 as the thickness of the interposer 110 is increased from 240 μm to 400 μm, and the stress on the chip-connecting surface 111 increases, though not by as much as in (A). As shown in (C), the absolute value of the sum of the stress (sometimes referred to as the "second stress") due to the axial force of the interposer 110 and the stress (sometimes referred to as the "third stress") due to the warpage of the interposer 110 on the chip-connecting surface 111 is minimized when the thickness of the interposer 110 is from 200 μm to 240 μm, and the first stress on the chip-connecting surface 111 is minimized. Therefore, the first stress on the chip-connecting surface 111 can be minimized by setting the thickness of the interposer 110 from 200 μm to 240 μm with respect to a predetermined supporting substrate 105 and joined layer. The present invention proposes a method for determining the thickness of an interposer able to minimize the first stress on the chip-connecting surface 111 on the basis of these findings.

Figure 4:
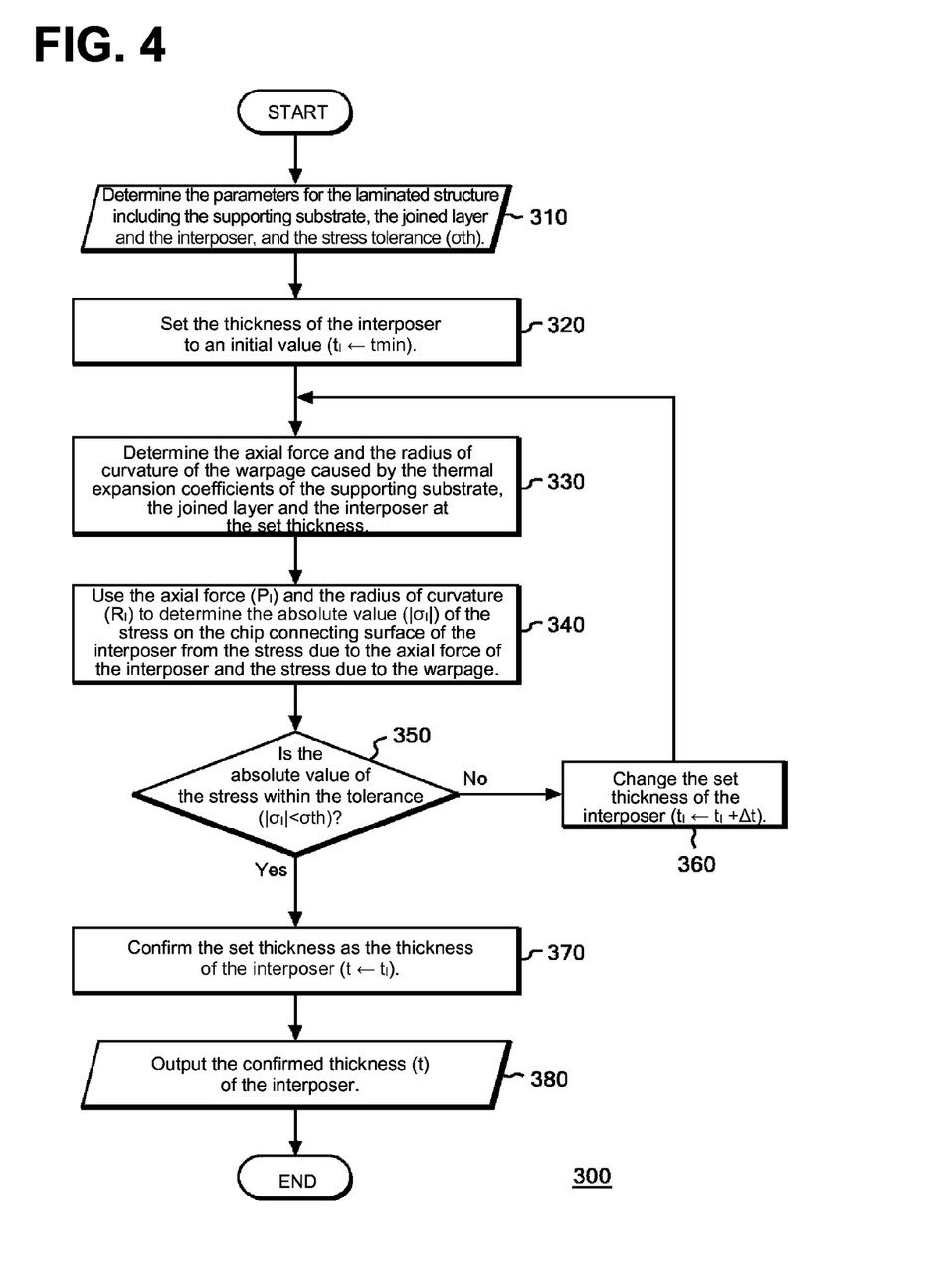
FIG. 4 is a flowchart showing the method used to determine the thickness of an interposer in an embodiment of the present invention.

FIG. 4 is a flowchart showing the method 300 used to determine the thickness of an interposer in an embodiment of the present invention. When the process has been initiated, data is prepared for the supporting substrate, the joined layer, and the interposer in Step 310. Examples of prepared data include: the Young's modulus ($E_S$, $E_C$, $E_I$) and thermal expansion coefficients ($\alpha_S$, $\alpha_C$, $\alpha_I$) of the supporting substrate, the joined layer, and the interposer; the desired thicknesses ($t_S$, $t_C$) of the supporting substrate and the joined layer; the minimum initial value (tmin) and the change ($\Delta t$) in the thickness of the interposer; and parameters for the laminated structure including the supporting substrate, the joined layer, and the interposer, such as the width ($b_S$, $b_C$, $b_I$) and length ($L_S$, $L_C$, $L_I$) of each and the stress tolerance (σth).

In Step 320 (see FIG. 4), the thickness ($t_I$) of the interposer is set to an initial value (tmin) ($t_I \leftarrow$ tmin). In Step 330, the axial force ($P_I$) and the radius of curvature of the warpage ($R_I$) of the interposer caused by the thermal expansion coefficients ($\alpha_S$, $\alpha_C$, $\alpha_I$) of the supporting substrate, the joined layer and the interposer at the set thickness ($t_I$) are determined. In Step 340, the determined axial force ($P_I$) and the radius of curvature ($R_I$) are used to determine the absolute value ($|\sigma_I|$) of the first stress on the chip-connecting surface of the interposer from the second stress due to the axial force of the interposer and the third stress due to the warpage. In Step 350, it is determined whether or not the absolute value ($|\sigma_I|$) of the stress is within the tolerance (σth) ($|\sigma_I|$<σth).

When the absolute value ($|\sigma_I|$) of the stress is not within the tolerance (σth) in Step 350, the thickness ($t_I$) of the interposer is changed by a predetermined value ($\Delta t$) ($t_I \leftarrow t_I + \Delta t$) in Step 360 and the following steps are repeated: determining the axial force ($P_I$) and the radius of curvature ($R_I$) of the warpage of the interposer (330), determining the absolute value ($|\sigma_I|$) of the stress on the chip-connecting surface of the interposer (340), and determining whether or not the absolute value ($|\sigma_I|$) of the stress is within the tolerance (σth) (350). When the absolute value ($|\sigma_I|$) of the stress is within the tolerance (σth) in Step 350, the thickness ($t_I$) of the interposer is confirmed as the thickness (t) of the interposer in Step 370 (t←$t_I$). The confirmed thickness (t) of the interposer is outputted in Step 380, and the process is ended.

Figure 5:
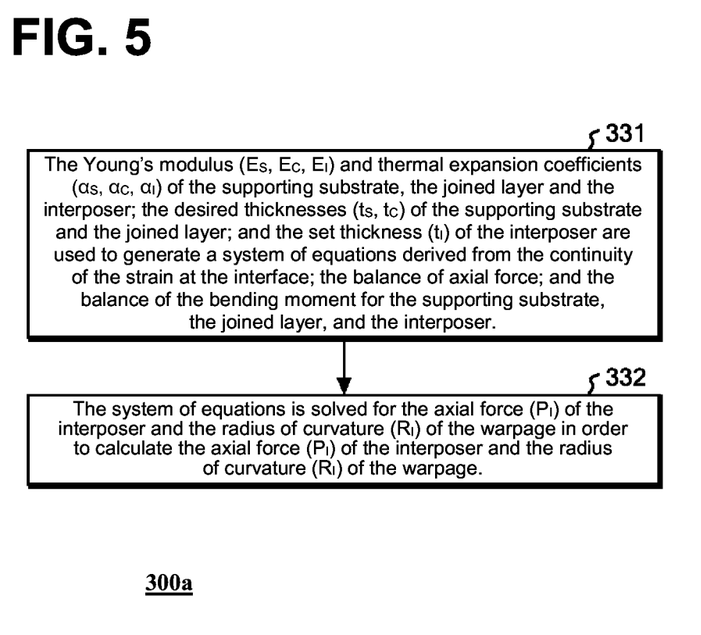
FIG. 5 is a flowchart showing Step 330 in FIG. 4.

FIG. 5 is a flowchart 300a showing Step 330 (see FIG. 4). In Step 331 (see FIG. 5), the Young's modulus ($E_S$, $E_C$, $E_I$) and thermal expansion coefficients ($\alpha_S$, $\alpha_C$, $\alpha_I$) of the supporting substrate, the joined layer, and the interposer; the desired thicknesses ($t_S$, $t_C$) of the supporting substrate and the joined layer; and the set thickness ($t_I$) of the interposer are used to generate a system of equations derived from the continuity of the strain at the interface; the balance of axial force; and the balance of the bending moment for the supporting substrate, the joined layer, and the interposer.

The continuity of the strain at the interface is established using the interface between layer 1 and layer 2 using Equation 1 below.

$$\alpha_1 T + \frac{P_1}{b_1 t_1 E_1} - \frac{t_1}{2R_1} = \alpha_2 T + \frac{P_2}{b_2 t_2 E_2} + \frac{t_2}{2R_2} \quad \text{(Eq. 1)}$$

$$\rightarrow (\alpha_1 - \alpha_2)T = -\frac{P_1}{b_1 t_1 E_1} + \frac{P_2}{b_2 t_2 E_2} + \frac{t_1}{2R_1} + \frac{t_2}{2R_2}$$

Variable T in Equation 1 is the change value for the temperature (° C.). Because the other variables have already been derived, explanation of these variables has been omitted. Subscripts 1 and 2 of the variables correspond to layer 1 and layer 2. For example, if layer 1 is the supporting substrate and layer 2 is the joined layer, subscript 1 for each variable is S and subscript 2 for each variable is C for the interface between the supporting substrate and the joined layer. Similarly, if layer 1 is the joined layer and layer 2 is the interposer, subscript 1 for each variable is C and subscript 2 for each variable is I for the interface between the joined layer and the interposer. Because the relationship in Equation 1 has been established both for the interface between the supporting substrate and the joined layer and for the interface between the joined layer and the interposer, Equation 1 is used.

The balance of the axial force between the layers 1, 2, 3, ... n is established using Equation 2 below.

$$\sum_i^n P_i = 0 \quad \text{(Eq. 2)}$$

$$0 = P_1 + P_2 \ldots + P_n$$

In Equation 2, the subscripts 1, 2, 3 ... n for axial force variable P correspond to layers 1, 2, 3, ... n. For example, if the supporting substrate, the joined layer and the interposer are layers 1, 2 and 3, respectively, the subscripts 1, 2 and 3 for variable P are S, C and I. Because the relationships in Equation 2 have been established between the supporting substrate, the joined layer, and the interposer, Equation 2 is used.

The balance of the bending moment between the layers 1, 2, 3, ... n is established using Equation 3 below.

$$\sum_i^n M_i + P_1\left(\bar{y} - \frac{t_1}{2}\right) + \quad \text{(Eq. 3)}$$

$$P_2\left(\bar{y} - t_1 - \frac{t_2}{2}\right) + \ldots + P_n\left(\bar{y} - t_1 - t_2 \ldots - \frac{t_n}{2}\right) = 0$$

$$\rightarrow 0 = P_1\left(\bar{y} - \frac{t_1}{2}\right) + P_2\left(\bar{y} - t_1 - \frac{t_2}{2}\right) + \ldots +$$

$$P_n\left(\bar{y} - t_1 - t_2 \ldots - \frac{t_n}{2}\right) + \frac{\sum_i^n E_i I_i}{R}$$

In Equation 3, Mi is the bending moment occurring in layer i. This is provided by Equation 4 below.

$$M_i = \frac{E_i I_i}{R_i} \quad \text{(Eq. 4)}$$

In Equation 4, Ei and Ri are the Young's modulus and the radius of curvature that have already been derived for layer i. Ii is the moment of inertia for layer i. Radii of curvature R1, R2, ... Rn are nearly equal and provided by Equation 5 below.

$$R_1 \cong R_2 \cong \ldots \cong R_n = R \quad \text{(Eq. 5)}$$

Therefore, Mi is expressed by EiIi/R. Referring to Equation 3, the overlined y indicates the position of the midplane of layer i. Because the relationships between the supporting substrate, the joined layer and the interposer are established by Equation 3, Equation 3 is used.

In Step 332 (see FIG. 5), the system of equations including Equation 1, Equation 2 and Equation 3 is solved in which the axial force ($P_I$) of the interposer and the radius of curvature ($R_I$) of the warpage are generated using each variable related the supporting substrate, the joined layer, and the interposer in order to calculate the axial force ($P_I$) of the interposer and the radius of curvature ($R_I$) of the warpage.

A general composite equation is used to calculate the Young's modulus ($E_C$) and the thermal expansion coefficient ($\alpha_C$) of the joined layer. The material properties of the composite can be determined using commercially available software. The general composite equation is expressed as follows. The physical values in the direction perpendicular to the direction of lamination, that is, the Young's modulus ($E\perp$) and the thermal expansion coefficient ($\alpha\perp$), are provided by Equation 6 below.

$$E_\perp = \frac{1}{V_F/E_F + (1-V_F)/E_M} \quad \text{(Eq. 6)}$$

$$\alpha_\perp = \alpha_M(1 - V_F) + \alpha_F V_F$$

The physical values in the direction parallel to the direction of lamination, that is, the Young's modulus ($E\|$) and the thermal expansion coefficient ($\alpha\|$), are provided by Equation 7 below.

$$E_\| = V_F E_F + (1 - V_F) E_M \quad \text{(Eq. 7)}$$

$$\alpha_\| = \frac{\alpha_M E_M (1-V_F) + \alpha_F E_F V_F}{E_M(1 - V_F) + E_F V_F}$$

In Equation 6 and Equation 7, V is the volume fraction, subscript M indicates the primary material, and subscript F indicates the secondary material. Therefore, in Equation 6 and Equation 7, the Young's modulus ($E\perp$) and the thermal expansion coefficient ($\alpha\perp$) in the direction perpendicular to the direction of lamination and the Young's modulus ($E\|$) and the thermal expansion coefficient ($\alpha\|$) in the direction parallel to the direction of lamination are determined using the Young's modulus ($E_M$) and the thermal expansion coefficient ($\alpha_M$) of the primary material in the joined layer, and the volume fraction (VF), the Young's modulus ($E_F$) and the thermal expansion coefficient ($\alpha_F$) of the secondary material.

Figure 6:
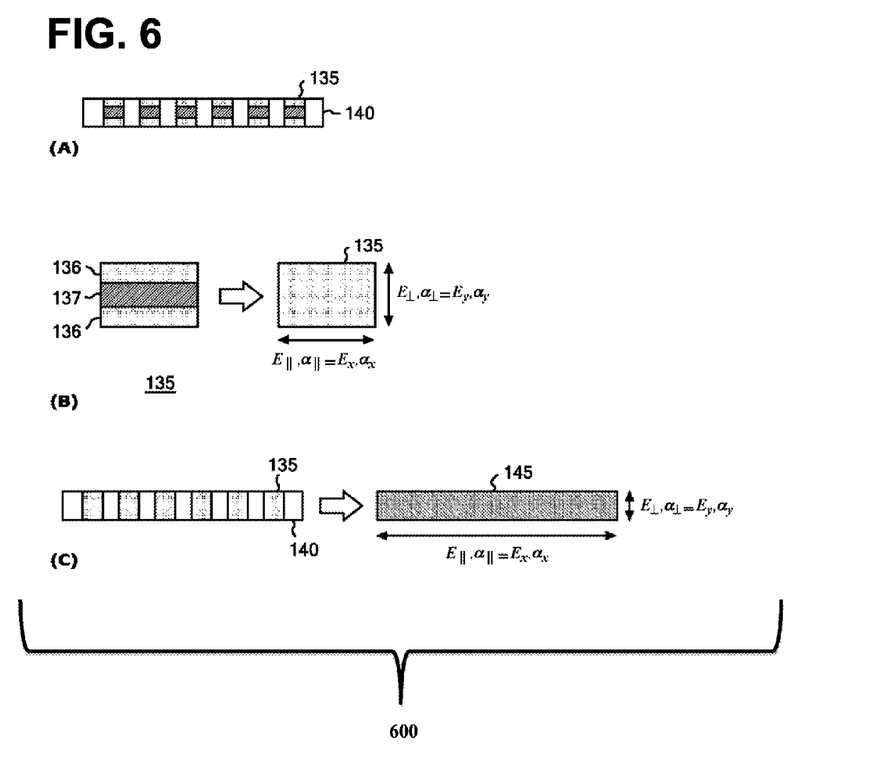
FIG. 6 is a simplified cross-sectional view of the preferred structure for the joined layer.

FIG. 6 is a simplified cross-sectional view 600 of the preferred structure for the joined layer. As shown in (A), the joined layer includes electrodes 135 and an underfill 140. Also, as shown in (B), the electrodes 135 have pads 136 of a metal such as copper (Cu) and bumps 137 of a copper-tin (CuSn) intermetallic compound (IMC). Using the Young's moduli and thermal expansion coefficients of the primary material and the secondary material constituting the electrode 135 and the volume fraction of the secondary material, the Young's modulus (E⊥) and the thermal expansion coefficient (α⊥) in the direction perpendicular (y) to the direction of lamination of the electrodes 135 and the Young's modulus (E∥) and the thermal expansion coefficient (α∥) in the direction (x) parallel to the direction of lamination from Equation 6 and Equation 7. When the Young's modulus (E⊥) and the thermal expansion coefficient (α⊥) in the direction perpendicular (y) to the direction of lamination of the electrodes 135 and the Young's modulus (E∥) and the thermal expansion coefficient (α∥) in the direction (x) parallel to the direction of lamination have been determined, Equation 6 and Equation 7 can be applied to the composite between the electrodes 135 and the underfill 140 as shown in (C) to determine the Young's modulus (E⊥) and the thermal expansion coefficient (α⊥) in the direction perpendicular (y) to the direction of lamination of the joined layer 145 constituted by the electrodes 135 and the underfill 140 and the Young's modulus (E∥) and the thermal expansion coefficient (α∥) in the direction (x) parallel to the direction of lamination.

Figure 7:
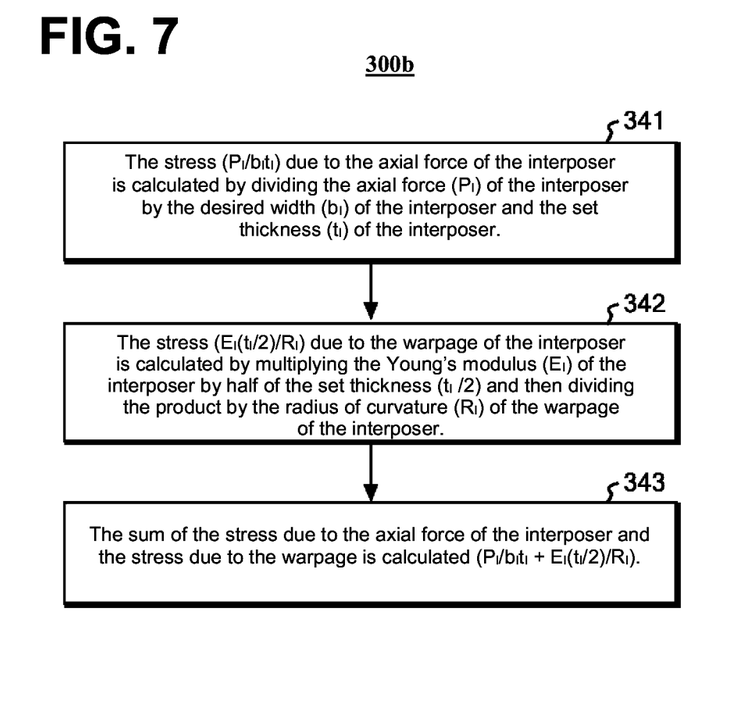
FIG. 7 is a flowchart showing Step 340 in FIG. 4.

FIG. 7 is a flowchart 300b showing Step 340 (see FIG. 4). In Step 341, the stress ($P_I/b_I t_I$) due to the axial force of the interposer is calculated by dividing the axial force ($P_I$) of the interposer by the desired width ($b_I$) of the interposer and the set thickness ($t_I$) of the interposer. The axial force ($P_I$) of the interposer is the value derived in Step 330 (see FIG. 4) and, more specifically, the value calculated in Steps 331 and 332 (see FIG. 5). The desired width ($b_I$) of the interposer and the set thickness ($t_I$) of the interposer are determined beforehand. In Step 342 (see FIG. 7), the stress ($E_I(t_I/2)/R_I$) due to the warpage of the interposer is calculated by multiplying the Young's modulus ($E_I$) of the interposer by half of the set thickness ($t_I/2$) and then dividing the product by the radius of curvature ($R_I$) of the warpage of the interposer. The radius of curvature ($R_I$) of the warpage of the interposer is the value derived in Step 330 and, more specifically, the value calculated in Steps 331 and 332. The Young's module ($E_I$) and the set thickness ($t_I$) of the interposer are determined beforehand. In Step 343, the sum of the stress due to the axial force of the interposer and the stress due to the warpage is calculated ($P_I/b_I t_I + E_I(t_I/2)/R_I$). The stress ($P_I/b_I t_I$) due to the axial force of the interposer is the value calculated in Step 341 and the stress ($E_I(t_I/2)/R_I$) due to the warpage of the interposer is the value calculated in Step 342.

A method for determining the thickness of an interposer according to an embodiment of the present invention is shown in FIG. 4 through FIG. 7. However, the present invention can be embodied as a computer program. A computer program can be created to enable a computer to execute each step in the method. In this embodiment, the computer program is stored in the storage device of a computer such as memory or a hard disk, and the computer program stored in the storage device is read and commands are issued by a processing device such as a central processing unit (CPU).

Figure 8:
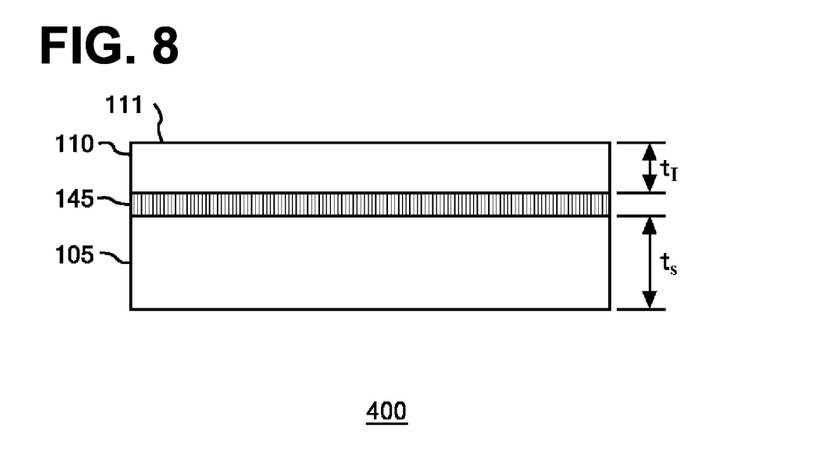
FIG. 8 is a simplified side view of the interposer being used in an embodiment of the present invention.

FIG. 8 is a simplified side view of an interposer 400 being used in an embodiment of the present invention. When the Young's modulus ($E_S$, $E_C$, $E_I$) and thermal expansion coefficients ($α_S$, $α_C$, $α_I$) of the supporting substrate, the joined layer, and the interposer, and the desired thicknesses ($t_S$, $t_C$) of the supporting substrate and the joined layer are given, the thickness ($t_I$) of an interposer 110 able to minimize stress on the chip-connecting surface 111 is determined using the method for determining the thickness of an interposer according to the embodiment of the present invention described above (the present method). An interposer 110 created after determining its thickness in this way can be sold as a stand-alone product. In the configuration of the interposer 400 shown here, a chip has not yet been mounted. However, a supporting substrate 105 can be connected via a joined layer 145 to the reverse surface of an interposer 110 created after determining its thickness in this way, and the resulting assembly can be sold as a product.

Figure 9:
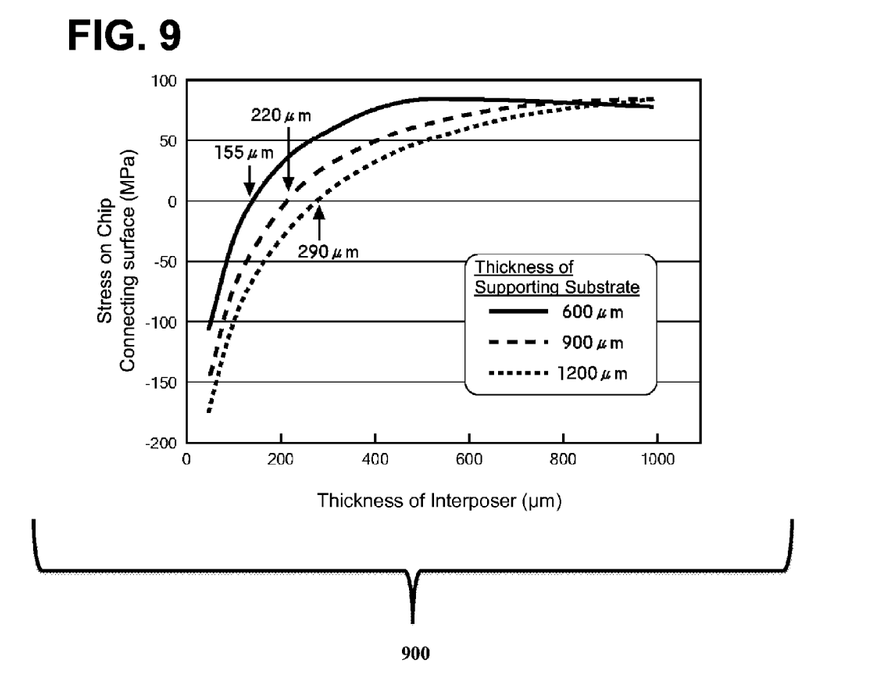
FIG. 9 is a graph showing the relationship between the thickness of the interposer and the stress on the chip-connecting surface in an embodiment of the present invention.

FIG. 9 is a graph 900 showing the relationship between the thickness of the interposer 400 and the stress on the chip-connecting surface in an embodiment of the present invention. When the thicknesses of the organic supporting substrates 105 are 600 μm, 900 μm and 1200 μm, the stress (MPa) on the chip-connecting surface 111 of a silicon interposer 110 changes from a negative value to a positive value via zero as the thickness (μm) increases. The thickness of the interposer determined using the method of the present invention (the present method) is a thickness approximate to the thickness at which the stress on the chip-connecting surface 111 is zero. If the stress tolerance (σth) is as small as possible, the thickness ($t_I$) of the interposer can be set as close as possible to the thickness at which the stress on the chip-connecting surface 111 is zero. The thicknesses of the silicon interposers 110 determined using the present method are 155 μm, 220 μm and 290 μm, respectively, for organic supporting substrates 105 with thicknesses of 600 μm, 900 μm and 1200 μm.

Figure 10:
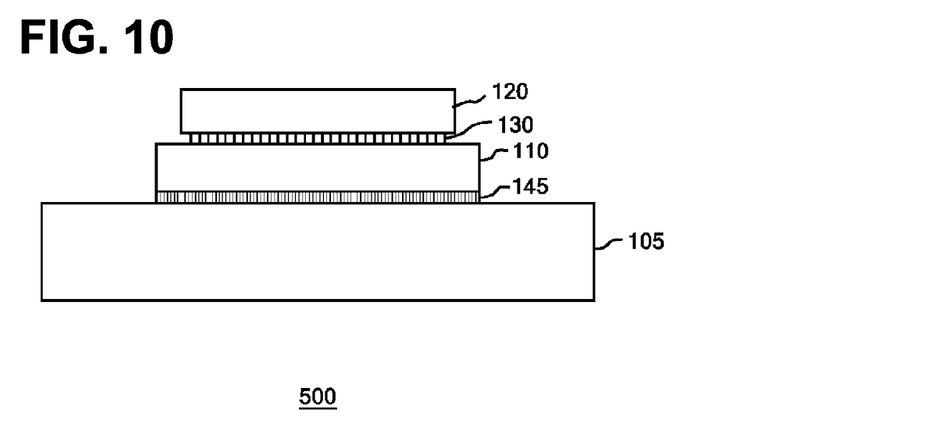
FIG. 10 is a simplified cross-sectional view of a chip mounting structure analyzed using FEM.

FIG. 10 is a simplified cross-sectional view of a chip mounting structure 500 analyzed using FEM. In this chip mounting structure 500, unlike the chip mounting structure 100 in FIG. 1, a top chip 120 is mounted directly on the obverse surface of the interposer 110 and not via a laminated chip 115. In order to facilitate comparison of this structure to the interposer configuration 400 according to the embodiment of the present invention shown in FIG. 8, the Young's modulus ($E_S$, $E_C$, $E_I$) and thermal expansion coefficients ($α_S$, $α_C$, $α_I$) of the supporting substrate, the joined layer, and the interposer, and the desired thicknesses ($t_S$, $t_C$) of the supporting substrate and the joined layer are the same.

Figure 11:
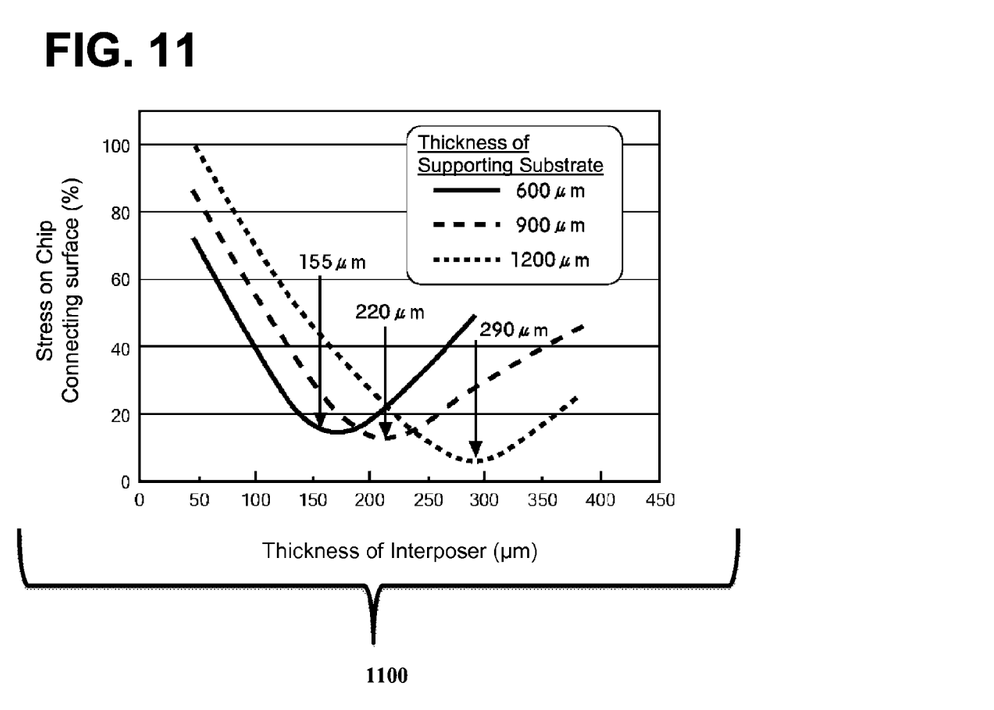
FIG. 11 is a graph showing the relationship between the thickness of the interposer and the stress on the chip-connecting surface as analyzed using FEM in FIG. 10.

FIG. 11 is a graph 1100 showing the relationship between the thickness of the interposer 110 in a chip mounting structure 500 and the stress on the chip-connecting surface as analyzed using FEM. In an FEM analysis, the stress (%) on the chip mounting surface of a silicon interposer 110 is minimized in the ranges 140-190 μm, 200-240 μm and 270-330 μm, respectively, when the organic supporting substrates 105 have thicknesses of 600 μm, 900 μm and 1200 μm. As shown in FIG. 11, the thicknesses 155 μm, 220 μm, 290 μm determined using the method for determining the thickness of an interposer according to the embodiment of the present invention (the present method) are within the thickness ranges for the interposer 110 determined by FEM analysis to minimize stress on the chip-connecting surface. Therefore, when a predetermined joined layer is used and the thicknesses of the organic supporting substrates 105 are 600 μm, 900 μm and 1200 μm, silicon interposers 110 having thicknesses of 155 μm, 220 μm and 290 μm as determined by the present method have been confirmed as being able to minimize the stress on the chip mounting surface.

Figure 12:
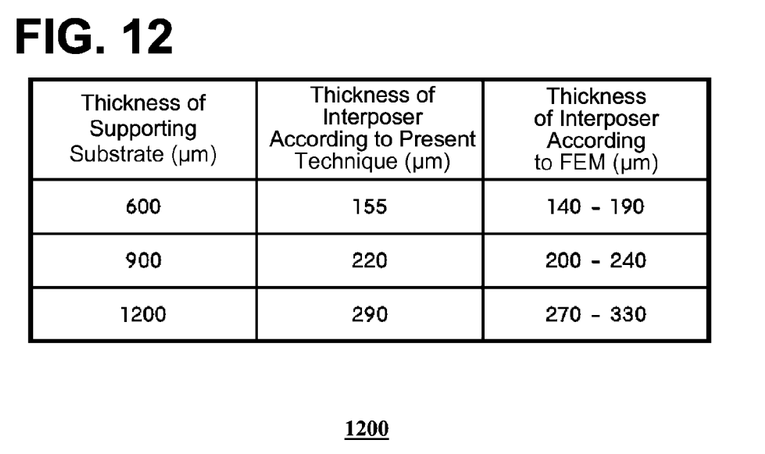
FIG. 12 is a table showing the thickness of the interposer for supporting substrates of varying thicknesses as determined by the present technique and by FEM.

FIG. 12 is a table 1200 for comparative purposes showing the thickness of a silicon interposer 110 as determined by the technique of the present invention and the thickness range of the interposer 110 for minimizing the stress on the chip-connecting surface as determined using FEM for organic supporting substrates 105 having a thickness of 600 µm, 900 µm and 1200 µm.

The present invention was explained above using an embodiment, but the technical scope of the present invention is not limited in any way by the embodiment. It should be clear that various modifications and improvements can be made, and that embodiments including these modifications and improvements are included in the technical scope of the present invention.

What is claimed is:

1. A chip mounting structure comprising:
a flip chip,
an interposer whose obverse surface is connected to the flip chip,
a supporting substrate connected to the reverse surface of the interposer, and
a joined layer provided between the interposer and the supporting substrate,
wherein the thickness of the interposer is determined by:
    setting the thickness of the interposer to an initial value;
    determining an axial force of the interposer and a radius of curvature of a warpage caused by a difference in thermal expansion coefficients of the supporting substrate, the joined layer, and the interposer at the set thickness;
    determining, using the determined axial force and radius of curvature, the absolute value of a first stress on a chip-connecting surface of the interposer from a second stress due to the axial force of the interposer and a third stress due to the warpage;
    determining whether the absolute value of the first stress is within a tolerance;
    changing the thickness of the interposer by a predetermined value, when the determined absolute value of the first stress is not within the tolerance, and repeating the steps of determining the axial force of the interposer and the radius of curvature, determining the absolute value of the first stress on the chip-connecting surface of the interposer, and determining whether the determined absolute value of the first stress is within the tolerance; and
    confirming the set thickness as the thickness of the interposer when determined absolute value of the first stress is within the tolerance.

2. The chip mounting structure of claim 1, wherein determining the axial force of the interposer and the radius of curvature of the warpage further comprises:
    generating a system of equations derived from the continuity of the strain at the interface for, the balance of axial force for, and the balance of the bending moment for the supporting substrate, the joined layer, and the interposer; and
    calculating the axial force and the radius of curvature of the warpage by solving the system of equations for an axial thrust of the interposer and the radius of curvature of the warpage;
    wherein the system of equations is generated using:
        the Young's modulus and thermal expansion coefficient of the supporting substrate, the joined layer, and the interposer;
        the desired thickness of the supporting substrate and the joined layer; and
        the set thickness of the interposer.

3. The chip mounting structure of claim 2, wherein the Young's modulus and the thermal expansion coefficient of the joined layer are the Young's modulus and the thermal expansion coefficient calculated from the metal properties of a complex between a metal joined portion and an underfill resin portion.

4. The chip mounting structure according of claim 1, wherein determining the absolute value of the stress on the chip-connecting surface of the interposer further comprises:
    calculating a second stress due to the axial force of the interposer by dividing the axial force of the interposer by a desired width of the interposer and the set thickness;
    calculating a third stress due to the warpage of the interposer by multiplying the Young's modulus of the interposer by half of the set thickness, and dividing the product by the radius of curvature of the warpage of the interposer; and
    calculating the total stress due to the axial force of the interposer and the third stress due to the warpage.

5. The chip mounting structure of claim 1, wherein the interposer is a silicon interposer, and the supporting substrate is an organic substrate.

6. A method comprising:
    setting the thickness of an interposer to an initial value, where the interposer is connected via a joined layer to a supporting substrate;
    determining an axial force of the interposer and a radius of curvature of a warpage caused by a difference in thermal expansion coefficients of the supporting substrate, the joined layer, and the interposer at the set thickness;
    determining, using the determined axial force and radius of curvature, the absolute value of a first stress on a chip-connecting surface of the interposer from a second stress due to the axial force of the interposer and a third stress due to the warpage;
    determining whether the absolute value of the first stress is within a tolerance;
    changing the thickness of the interposer by a predetermined value, when the determined absolute value of the first stress is not within the tolerance, and repeating the steps of determining the axial force of the interposer and the radius of curvature, determining the absolute value of the first stress on the chip-connecting surface of the interposer, and determining whether the determined absolute value of the first stress is within the tolerance; and
    confirming the set thickness as the thickness of the interposer when the determined absolute value of the first stress is within the tolerance.

7. The method of claim 6, wherein the step of determining the axial force of the interposer and the radius of curvature of the warpage further comprises the steps of:
    generating a system of equations derived from the continuity of the strain at the interface, the balance of axial force, and the balance of the bending moment for the supporting substrate, the joined layer, and the interposer; and
    calculating the axial force and the radius of curvature of the warpage by solving the system of equations for an axial thrust of the interposer and the radius of curvature of the warpage;

wherein the system of equations is generated using:
the Young's modulus and thermal expansion coefficient of the supporting substrate, the joined layer, and the interposer;
the desired thickness of the supporting substrate and the joined layer; and
the set thickness of the interposer.

8. The method of claim 7, wherein the Young's modulus and the thermal expansion coefficient of the joined layer are the Young's modulus and the thermal expansion coefficient calculated from the metal properties of a complex between a metal joined portion and an underfill resin portion.

9. The method of claim 6, wherein the step of determining the absolute value of the stress on the chip-connecting surface of the interposer further comprises the steps of:
calculating a second stress due to the axial force of the interposer by dividing the axial force of the interposer by a desired width of the interposer and the set thickness;
calculating a third stress due to the warpage of the interposer by multiplying the Young's modulus of the interposer by half of the set thickness, and dividing the product by the radius of curvature of the warpage of the interposer; and
calculating the total stress due to the axial force of the interposer and the third stress due to the warpage.

10. An interposer connected via a joined layer to a supporting substrate, the thickness of the interposer being determined by:
setting the thickness of the interposer to an initial value;
determining an axial force of the interposer and a radius of curvature of a warpage caused by a difference in thermal expansion coefficients of the supporting substrate, the joined layer, and the interposer at the set thickness;
determining, using the determined axial force and radius of curvature, the absolute value of a first stress on a chip-connecting surface of the interposer from a second stress due to the axial force of the interposer and a third stress due to the warpage;
determining whether the absolute value of the first stress is within a tolerance;
changing the thickness of the interposer by a predetermined value, when the determined absolute value of the first stress is not within the tolerance, and repeating the steps of determining the axial force of the interposer and the radius of curvature, determining the absolute value of the first stress on the chip-connecting surface of the interposer, and determining whether the determined absolute value of the first stress is within the tolerance; and
confirming the set thickness as the thickness of the interposer when determined absolute value of the first stress is within the tolerance.

11. The interposer of claim 10, wherein determining the axial force of the interposer and the radius of curvature of the warpage further comprises:
generating a system of equations derived from the continuity of the strain at the interface, the balance of axial force, and the balance of the bending moment for the supporting substrate, the joined layer, and the interposer; and
calculating the axial force and the radius of curvature of the warpage by solving the system of equations for an axial thrust of the interposer and the radius of curvature of the warpage;
wherein the system of equations is generated using:
the Young's modulus and thermal expansion coefficient of the supporting substrate, the joined layer, and the interposer;
the desired thickness of the supporting substrate and the joined layer; and
the set thickness of the interposer.

12. The interposer of claim 11, wherein the Young's modulus and the thermal expansion coefficient of the joined layer are the Young's modulus and the thermal expansion coefficient calculated from the metal properties of a complex between a metal joined portion and an underfill resin portion.

13. The interposer of claim 10, wherein determining the absolute value of the stress on the chip-connecting surface of the interposer further comprises:
calculating a second stress due to the axial force of the interposer by dividing the axial force of the interposer by a desired width of the interposer and the set thickness;
calculating a third stress due to the warpage of the interposer by multiplying the Young's modulus of the interposer by half of the set thickness, and dividing the product by the radius of curvature of the warpage of the interposer; and
calculating the total stress due to the axial force of the interposer and the third stress due to the warpage.

* * * * *